(12) United States Patent
Helm et al.

(10) Patent No.: US 9,107,632 B2
(45) Date of Patent: *Aug. 18, 2015

(54) SYSTEM AND METHOD FOR OFF-CENTER IMAGING

(71) Applicant: Medtronic Navigation, Inc., Louisville, CO (US)

(72) Inventors: Patrick A. Helm, Milton, MA (US); Michael Connor, Tyngsboro, MA (US); Russell Stanton, Lunenburg, MA (US); Norbert Johnson, North Andover, MA (US); Eugene A. Gregerson, Bolton, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/058,864

(22) Filed: Oct. 21, 2013

(65) Prior Publication Data

US 2014/0050303 A1 Feb. 20, 2014

Related U.S. Application Data

(63) Continuation of application No. 13/075,446, filed on Mar. 30, 2011, now Pat. No. 8,562,211.

(51) Int. Cl.
*H05G 1/04* (2006.01)
*A61B 6/00* (2006.01)
(Continued)

(52) U.S. Cl.
CPC ............... *A61B 6/4447* (2013.01); *A61B 6/035* (2013.01); *A61B 6/4405* (2013.01); *A61B 6/4452* (2013.01); *A61B 6/4476* (2013.01); *A61B 6/469* (2013.01); *A61B 6/488* (2013.01);
(Continued)

(58) Field of Classification Search
USPC ................ 378/4–20, 193, 195, 196, 197, 198
See application file for complete search history.

(56) References Cited

U.S. PATENT DOCUMENTS 4,149,079 A * 4/1979 Ben-Zeev et al. ................. 378/9
6,940,941 B2 9/2005 Gregerson et al.
(Continued)

FOREIGN PATENT DOCUMENTS

JP H09-234192 9/1997
JP 2001-120533 A 5/2001
(Continued)

OTHER PUBLICATIONS

"Medtronic O-Arm Multi-Dimensional Surgical Imaging System"; Brochure, 24pp, 2009.
(Continued)

*Primary Examiner* — Hoon Song
(74) *Attorney, Agent, or Firm* — Harness, Dickey

(57) ABSTRACT

A system and a method for acquiring image data of a subject with an imaging system is provided. The system can include a gantry that completely annularly encompasses at least a portion of the subject, which can be positioned along at an isocenter of the imaging system. The system can include a source and a detector positioned within and movable relative to the gantry on a rotor. The system can include a move control module that sets move data for each of the source, detector and rotor that causes the source, detector and rotor to move in a desired motion profile to acquire image data of a portion of the subject off the isocenter of the imaging system.

20 Claims, 9 Drawing Sheets

(51) Int. Cl.
*A61B 6/03* (2006.01)
*A61B 6/12* (2006.01)
*A61B 6/02* (2006.01)
*A61B 19/00* (2006.01)

(52) U.S. Cl.
CPC ............... *A61B 6/545* (2013.01); *A61B 6/587* (2013.01); *A61B 6/027* (2013.01); *A61B 6/12* (2013.01); *A61B 19/5244* (2013.01)

(56) References Cited

U.S. PATENT DOCUMENTS

| | | | |
|---|---|---|---|
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 8,562,211 | B2 * | 10/2013 | Helm et al. .................. 378/197 |
| 2003/0076920 | A1 | 4/2003 | Shinno et al. |
| 2004/0013225 | A1 * | 1/2004 | Gregerson et al. ............. 378/19 |
| 2005/0053200 | A1 * | 3/2005 | Sukovic et al. ............... 378/210 |
| 2006/0140339 | A1 * | 6/2006 | Marcovitch .................... 378/20 |
| 2007/0230654 | A1 * | 10/2007 | Chappo et al. ................. 378/15 |
| 2010/0290690 | A1 | 11/2010 | Hartmann et al. |
| 2011/0033024 | A1 | 2/2011 | Dafni et al. |
| 2012/0250818 | A1 | 10/2012 | Helm et al. |

FOREIGN PATENT DOCUMENTS

| | | |
|---|---|---|
| JP | 2005-527800 A | 9/2005 |
| WO | WO-03081220 A2 | 10/2003 |
| WO | WO-2010041193 A2 | 4/2010 |
| WO | WO-2011001025 A1 | 1/2011 |
| WO | WO-2012135486 A1 | 10/2012 |

OTHER PUBLICATIONS

International Search Report and Written Opinion mailed Jun. 22, 2012 for PCT/US2012/031192 which claims benefit of U.S. Appl. No. 13/075,446, filed Mar. 30, 2011.

Office Action for Japanese Patent application No. 2014-502793 dated May 1, 2015 which corresponds to PCT/US2012/031192.

* cited by examiner

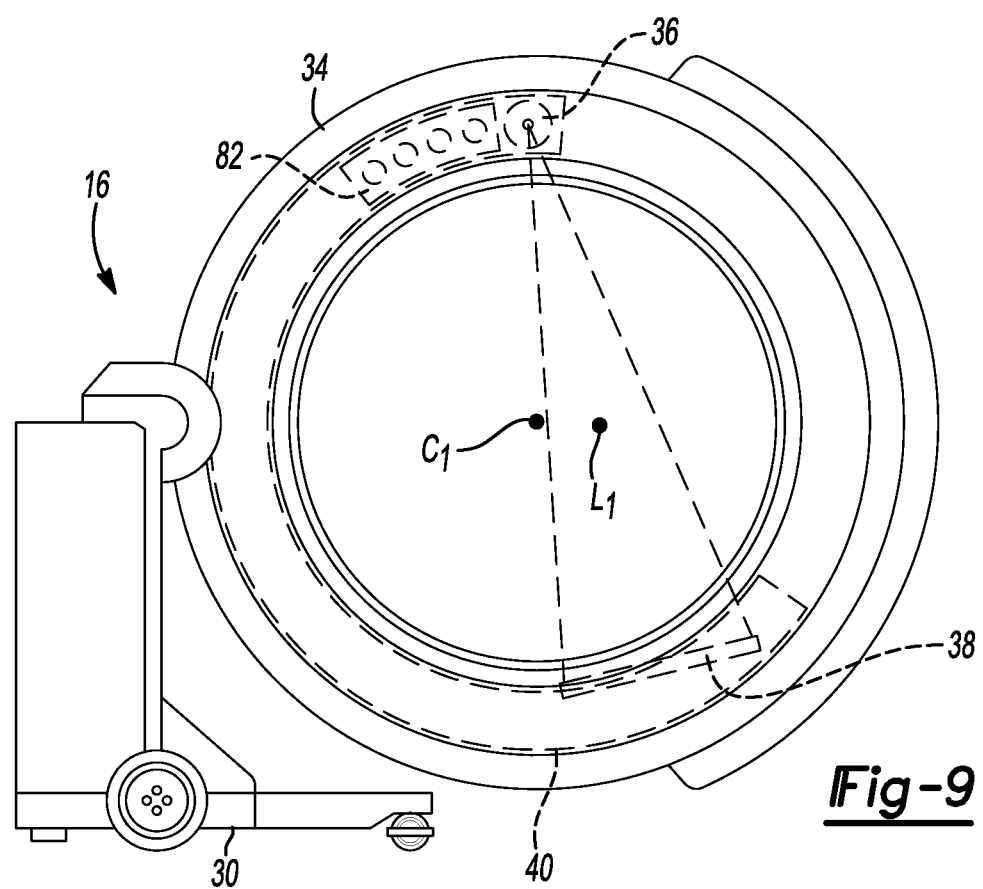

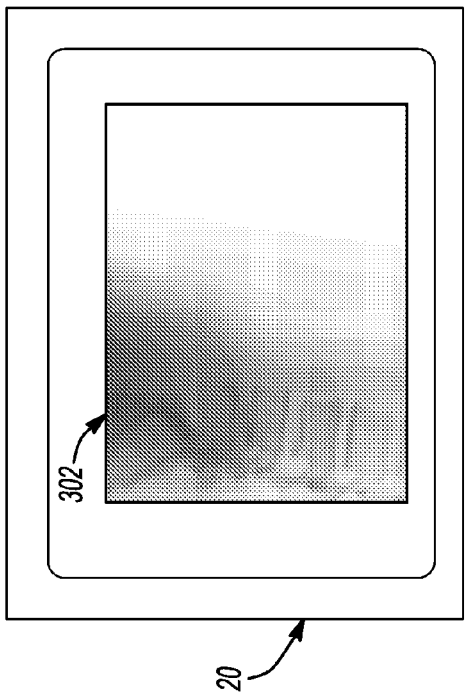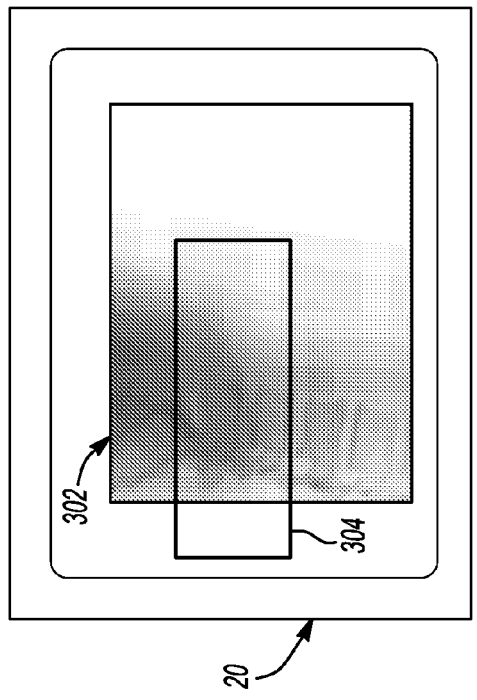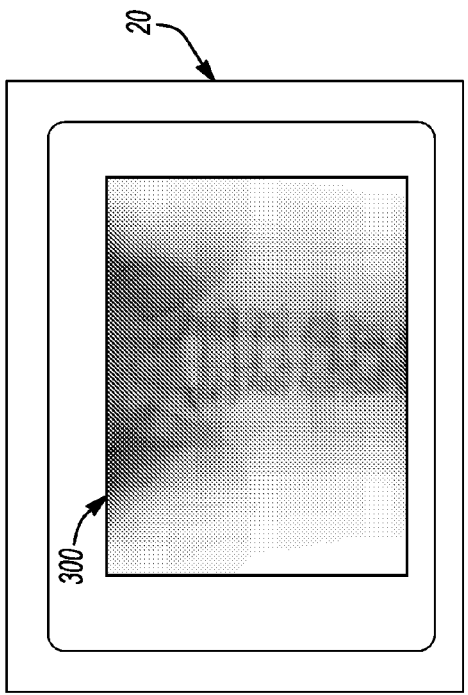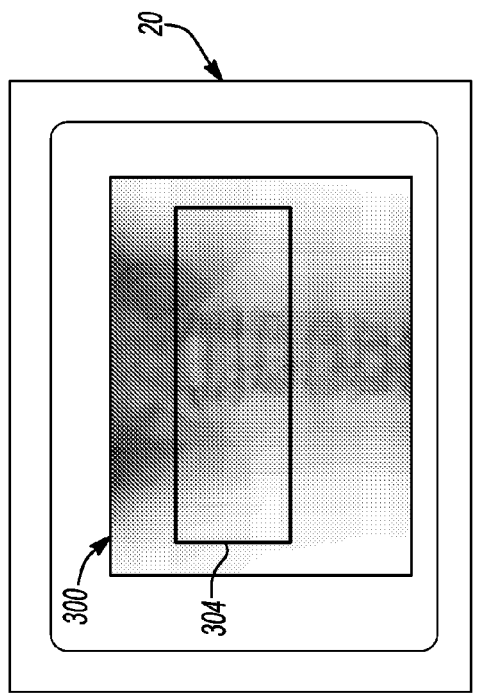

SYSTEM AND METHOD FOR OFF-CENTER IMAGING

CROSS-REFERENCE TO RELATED APPLICATIONS

This application is a continuation of U.S. application Ser. No. 13/075,446 filed on Mar. 30, 2011. The disclosure of the above application is incorporated herein by reference.

FIELD

The present disclosure relates to imaging a subject, and particularly to generating an image of a portion of a patient off-center from an isocenter of an imaging device.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

According to various embodiments, provided is a system for acquiring image data of a subject with an imaging system. The system can include a gantry that completely annularly encompasses at least a portion of the subject. The subject can be positioned along at an isocenter of the imaging system. The system can include a source positioned within and movable relative to the gantry. The source can be responsive to a signal to output at least one pulse. The system can include a detector positioned within and movable relative to the gantry and the source to detect the at least one pulse emitted by the source. The system can include a detector control module that sets detector data based on the detected at least one pulse, and a rotor positioned within the gantry and movable within the gantry. The source and the detector can be coupled to the rotor so as to be substantially opposed from each other. The source and the detector can be movable relative to the rotor. The system can include an image control module that sets the signal for the source and receives the detector data. The image control module can be operable to reconstruct image data based on the detector data. The system can include a move control module that sets move data for each of the source, detector and rotor that causes the source, detector and rotor to move in a desired motion profile to acquire the image data of a portion of the subject off the isocenter of the imaging system.

Further provided is a method for acquiring image data of a subject with an imaging system. The method can include providing a gantry operable to completely annularly encompass at least a portion of the subject, the subject positioned along an isocenter of the imaging system. The imaging system can include a source and a detector positioned within and coupled to a rotor movable relative to the gantry. The method can also include receiving at least one user input that provides a request for acquiring image data of a portion of the subject off-center from the isocenter of the imaging system, and determining, based on the user input, move data for the source, detector and rotor within the gantry to acquire the off-center image data. The method can include moving the source relative to the rotor based on the move data, and moving the detector relative to the rotor based on the move data. The method can also include moving the rotor relative to the gantry based on the move data, and outputting at least one pulse with the source. The method can include receiving the at least one pulse with the detector, and reconstructing, based on the at least one pulse received by the detector, an image of the subject.

Also provided is a method for acquiring image data of a subject with an imaging system. The method can include providing a gantry operable to completely annularly encompass at least a portion of the subject. The subject can be positioned along an isocenter of the imaging system, and the imaging system can include a source and a detector positioned within and coupled to a rotor movable relative to the gantry. The method can include receiving a first user input that provides a request for acquiring image data of a portion of the subject along the isocenter of the imaging system, and acquiring initial image data of the portion of the subject. The method can also include displaying the initial image data of the portion of the subject on a display, and receiving a second user input based on the displayed initial image data that includes a request to gather off-center image data of a portion of the subject off-center from the isocenter of the imaging device. The method can include determining, based on the second user input, move data for the source, detector and rotor within the gantry to acquire the off-center image data, and pivoting the source relative to the rotor based on the move data. The method can include pivoting the detector relative to the rotor based on the move data, and rotating the rotor relative to the gantry based on the move data.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 9 is a schematic illustration of the imaging system of FIG. 1, with the source and the detector of the imaging system in a fifth position;

FIG. 10A is an exemplary representation of an anterior-posterior image acquired by the imaging system of FIG. 1;

FIG. 10B is an exemplary representation of a lateral image acquired by the imaging system of FIG. 1;

FIG. 11A is an exemplary graphical representation of a selected location of interest selected on the anterior-posterior image FIG. 10A;

FIG. 11B is an exemplary graphical representation of a selected location of interest selected on the lateral image FIG. 10B;

DETAILED DESCRIPTION

Figure 1:
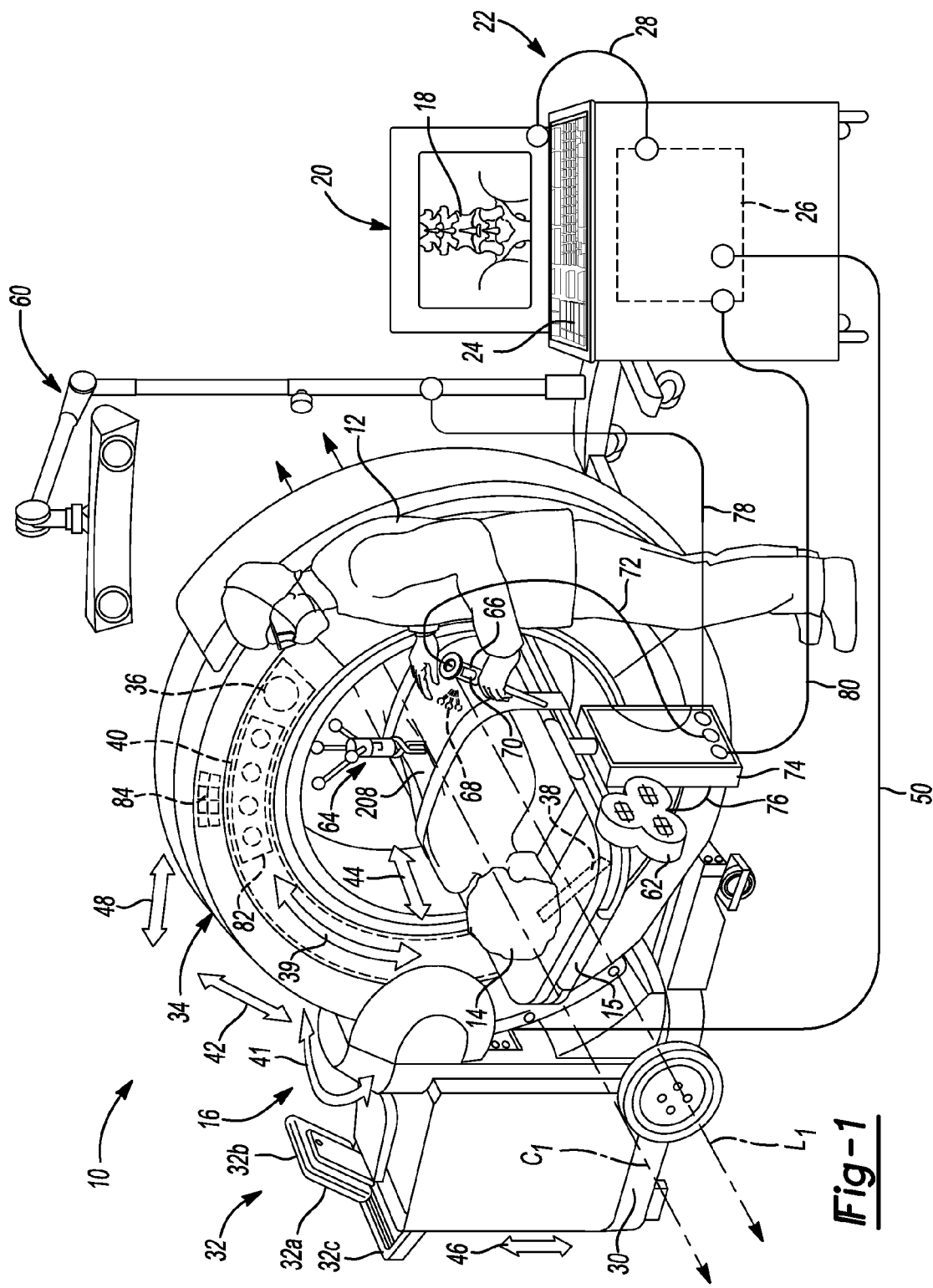
FIG. 1 is an environmental view of an exemplary imaging system in an operating theatre, with a source and a detector of the imaging system in a first position.

The following description is merely exemplary in nature. It should be understood that throughout the drawings, corresponding reference numerals indicate like or corresponding parts and features. As indicated above, the present teachings are directed toward off-center imaging for an imaging device, such as an O-Arm® imaging system sold by Medtronic Navigation, Inc. having a place of business in Louisville, Colo., USA. It should be noted, however, that the present teachings could be applicable to any appropriate imaging device, such as a C-arm imaging device. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

With reference to FIG. 1, in an operating theatre or operating room 10, a user, such as a user 12, can perform a procedure on a patient 14. In performing the procedure, the user 12 can use an imaging system 16 to acquire image data of the patient 14 for performing a procedure. The image data acquired of the patient 14 can include two-dimension (2D) projections acquired with an x-ray imaging system, including those disclosed herein. It will be understood, however, that 2D forward projections of a volumetric model can also be generated, also as disclosed herein.

In one example, a model can be generated using the acquired image data. The model can be a three-dimension (3D) volumetric model generated based on the acquired image data using various techniques, including algebraic iterative techniques, also as discussed further herein. Displayed image data 18 can be displayed on a display device 20, and additionally, could be displayed on a display device 32a associated with an imaging computing system 32, as will be discussed in greater detail herein. The displayed image data 18 can be a 2D image, a 3D image, or a time changing four-dimension image. The displayed image data 18 can also include the acquired image data, the generated image data, both, or a merging of both the types of image data.

It will be understood that the image data acquired of the patient 14 can be acquired as 2D projections, for example with an x-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a computing system 22. The computing system 22 can include a variety of computer-readable media. The computer-readable media can be any available media that can be accessed by the computing system 22 and can include both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can comprise any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 could comprise a touchpad or tablet computing device, and further, that the computing system 22 could be integrated within or be part of the imaging computing system 32 associated with the imaging system 16.

A connection 28 can be provided between the computing system 22 and the display device 20 for data communication to allow driving the display device 20 to illustrate the image data 18.

The imaging system 16 can include the O-Arm® imaging system sold by Medtronic Navigation, Inc. having a place of business in Louisville, Colo., USA. The imaging system 16, including the O-Arm® imaging system, or other appropriate imaging systems in use during a selected procedure are also described in U.S. patent application Ser. No. 12/465,206, entitled "System And Method For Automatic Registration Between An Image And A Subject," filed on May 13, 2009, incorporated herein by reference. Additional description regarding the O-Arm imaging system or other appropriate imaging systems can be found in U.S. Pat. Nos. 7,188,998, 7,108,421, 7,106,825, 7,001,045 and 6,940,941, each of which is incorporated herein by reference.

The O-Arm® imaging system 16 can include a mobile cart 30 that includes the imaging computing system 32 and an imaging gantry 34 in which is positioned a source unit 36 and a detector 38. With reference to FIG. 1, the mobile cart 30 can be moved from one operating theater or room to another and the gantry 34 can move relative to the mobile cart 30, as discussed further herein. This allows the imaging system 16 to be mobile so that it can be used in multiple locations and with multiple procedures without requiring a capital expenditure or space dedicated to a fixed imaging system.

Figure 2:
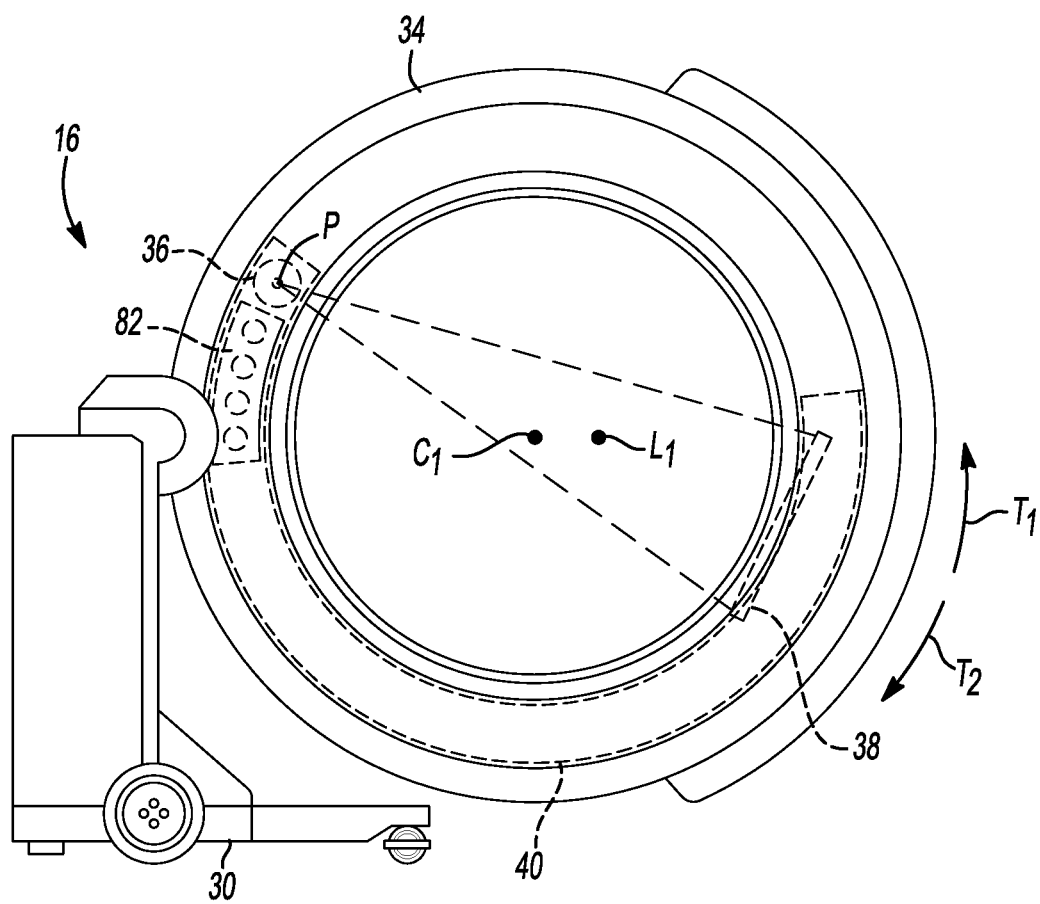
FIG. 2 is a schematic illustration of the imaging system of FIG. 1, with the source and the detector of the imaging system in a second position.

With reference to FIG. 2, the gantry 34 can define an isocenter of the imaging system 16. In this regard, a centerline C1 through the gantry 34 can define an isocenter or center of the imaging system 16, and any other line through the gantry 34, such as L1, can be considered to be off-isocenter or off-center of the imaging system 16. Generally, with reference to FIG. 1, the patient 14 can be positioned along the centerline C1 of the gantry 34, so that a longitudinal axis 14L of the patient 14 can be aligned with the isocenter of the imaging device 16. Image data acquired along the centerline C1 of the imaging device 16 can be considered isocenter or center image data, and image data acquired off-isocenter or off-center can be considered off-isocenter or off-center image data, as will be discussed herein.

Figure 3:
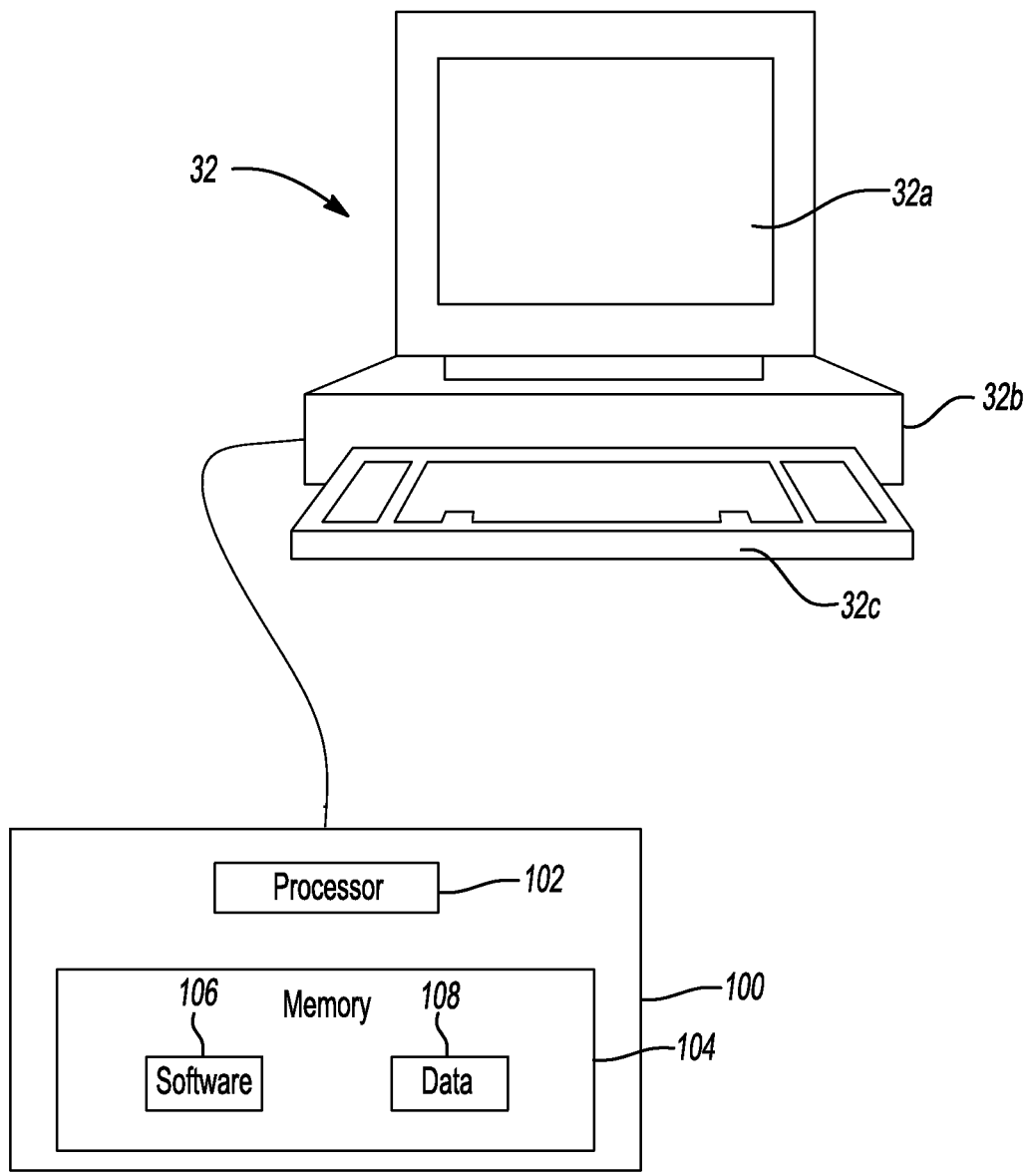
FIG. 3 is a schematic illustration of an exemplary computing system for use with the imaging system of FIG. 1.

With reference to FIG. 3, a diagram is provided that illustrates an exemplary embodiment of the imaging computing system 32, some or all of the components of which can be used in conjunction with the teachings of the present disclosure. The imaging computing system 32 can include a variety of computer-readable media. The computer-readable media can be any available media that can be accessed by the imaging computing system 32 and includes both volatile and nonvolatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 32. The computer-readable media may be accessed directly or through a network such as the Internet.

In one example, the imaging computing system 32 comprises a display device 32a and a system unit 32b. As illustrated, the display device 32a can comprise a computer video screen or monitor. The imaging computing system 32 can also include at least one input device 32c. The system unit 32b includes, as shown in an exploded view at 100, a processor 102 and a memory 104, which can include software 106 and data 108.

In this example, the at least one input device 32c comprises a keyboard. It should be understood, however, that the at least one input device 32c can comprise any suitable device to enable a user to interface with the imaging computing system 32, such as a touchpad, touch pen, touch screen, keyboard, mouse, joystick, trackball, wireless mouse, audible control or a combination thereof. Furthermore, while the imaging computing system 32 is described and illustrated herein as comprising the system unit 32b with the display device 32a, the imaging computing system 32 could comprise a touchpad or tablet computing device or use display 20.

As will be discussed with regard to FIGS. 4-9, the imaging computing system 32 can control the movement, positioning and adjustment of the source 36, the detector 38 and rotor 40 independently to enable off-center image data acquisition via an off-center image control module 110, which can each be stored in the memory 104 and accessed by the processor 102. A connection can be provided between the processor 102 and the display device 32a for data communication to allow driving the display device 32a to illustrate the image data 18.

Briefly, with reference to FIGS. 1 and 2, the source unit 36 can emit x-rays through the patient 14 to be detected by the detector 38. As is understood by one skilled in the art, the x-rays emitted by the source 36 can be emitted in a cone and detected by the detector 38. The source 36 and the detector 38 can each be coupled to the rotor 40 so as to be generally diametrically opposed within the gantry 34, and movable within the gantry 34 about the patient 14. Thus, the detector 38 can move rotationally in a 360° motion around the patient 14 generally in the directions of arrow 39, and the source 36 can move in concert with the detector 38 such that the source 36 remains generally 180° apart from and opposed to the detector 38.

In addition, with reference to FIG. 2, the source 36 can be pivotably mounted to the rotor 40 and controlled by an actuator, such that the source 36 can be controllably pivoted about its focal spot P relative to the rotor 40 and the detector 38. By controllably pivoting the source 36, the trajectory of the x-rays can be angled or altered relative to the patient 14, without requiring the patient 14 to be repositioned relative to the gantry 34. Further, the detector 38 can move about an arc relative to the rotor 40, in the direction of arrows T1 and T2. In one example, the detector 38 can pivot about the pivot about the focal spot P of the source 36, such that the source 36 and detector 38 can pivot about the same angle. As the detector 38 can pivot at the same angle as the source 36, the detector 38 can detect the x-rays emitted by the source 36 at any desired pivot angle, which can enable the acquisition of off-center image data as will be discussed further herein. The rotor 40 can be rotatable about the gantry 34 as needed to acquire the desired image data (on center or off-center). Additional details regarding the mechanics of the movement of the source 36, detector 38 and rotor 40 are disclosed in U.S. Pat. No. 7,108,421, incorporated by reference previously herein.

With reference to FIG. 1, the gantry 34 can isometrically sway or swing (herein also referred to as iso-sway) generally in the direction of arrow 41, relative to the patient 14, which can be placed on a patient support or table 15. The gantry 34 can also tilt relative to the patient 14 illustrated by arrows 42, move longitudinally along the line 44 relative to the patient 14 and the mobile cart 30, can move up and down generally along the line 46 relative to the mobile cart 30 and transversely to the patient 14, and move perpendicularly generally in the direction of arrow 48 relative to the patient 14 to allow for positioning of the source 36/detector 38 relative to the patient 14.

The O-Arm® imaging system 16 can be precisely controlled by the imaging computing system 32 to move the source 36 and the detector 38 relative to the patient 14 to generate precise image data of the patient 14. In addition, the imaging system 16 can be connected with the processor 26 via connection 50 which can include a wired or wireless connection or physical media transfer from the imaging system 16 to the processor 26. Thus, image data collected with the imaging system 16 can also be transferred from the imaging computing system 32 to the computing system 22 for navigation, display, reconstruction, etc.

Briefly, with continued reference to FIG. 1, according to various embodiments, the imaging system 16 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. If desired, the components associated with performing a navigated procedure could be integrated within the imaging device 16. The navigated space or navigational domain relative to the patient 14 can be registered to the image data 18 to allow registration of a navigation space defined within the navigational domain and an image space defined by the image data 18. A patient tracker or a dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74, which can communicate with the electromagnetic localizer 62 and/or the optical localizer 60. Using the communication lines 72, 78 respectively, the navigation interface device 74 can then communicate with the processor 26 with a communication line 80. It will be understood that any of the connections or communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 could be graphically illustrated as an icon superimposed on the image data 18.

Further, the imaging system 16 can include a tracking device, such as an optical tracking device 82 or an electromagnetic tracking device 84 to be tracked with a respective optical localizer 60 or the electromagnetic localizer 62. The tracking device 82, 84 can be associated directly with the source 36, the detector 38, rotor 40, the gantry 34, or other appropriate part of the imaging system 16 to determine the location or position of the source 36, detector 38, rotor 40 and/or gantry 34 relative to a selected reference frame. As illustrated, the tracking device 82, 84 can be positioned on the exterior of the housing of the gantry 34. Accordingly, the imaging system 16 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206.

Figure 4:
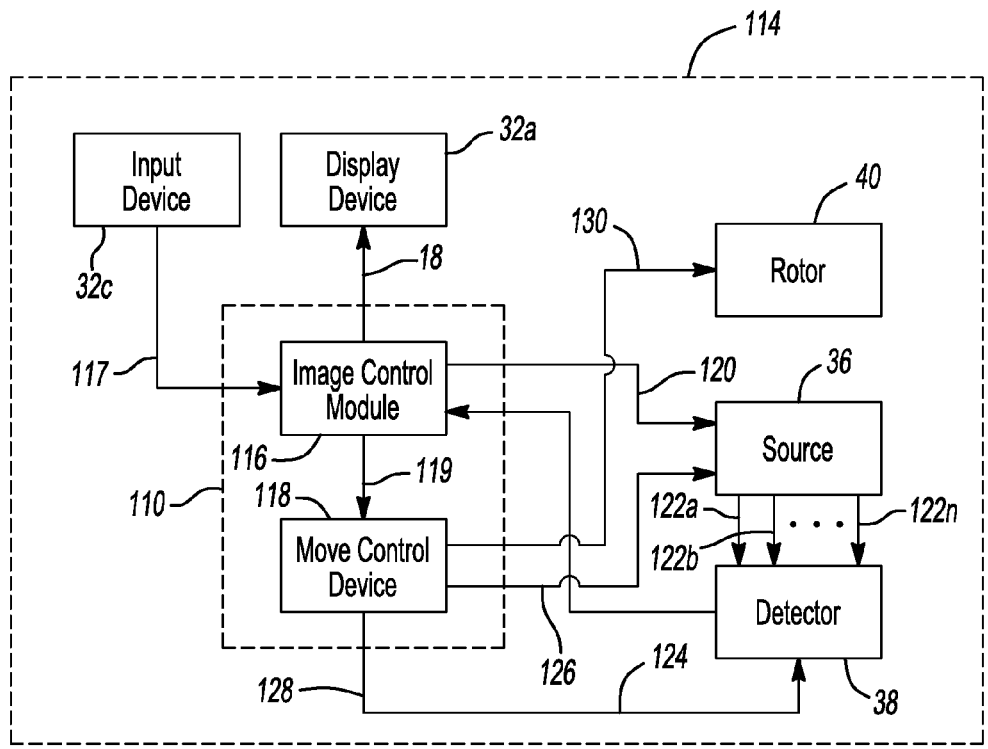
FIG. 4 is a simplified block diagram illustrating a system for implementing an off-center image control module according to various embodiments.

With reference to FIG. 4, a simplified block diagram schematically illustrates an exemplary system 114 for implementing the off-center image control module 110 according to various embodiments. In one example, the off-center image control module 110 can be implemented by the imaging computing system 32 of the imaging system 16. The off-center image control module 110 can include an image control module 116 and a move control module 118.

The image control module 116 can receive user input data 117 from the input device 32c and can output image data 18 to the display 32a. Note that while the display is illustrated and described herein as comprising the display device 32a, the imaging computing system 32 could output image data 18 to the display device 20. The user input data 117 can comprise a request to acquire initial images of the patient 14, and can also comprise a selected area of interest for additional imaging, as will be discussed herein. Based on the user input data 117, the image control module 116 can set a signal 119 to the move control module 118. The signal 119 can comprise a selected location on the patient 14 for the acquisition of image data.

The image control module 116 can also send a source signal 120 to the source 36. The source signal 120 can comprise a signal for the source 36 to output or emit at least one or more x-ray pulses $122a \ldots 122n$. The image control module 116 can also receive as in input a detector signal 124, which can comprise the x-ray pulses $122a \ldots 122n$ detected by the detector 38. Based on the received x-ray pulses $122a \ldots 122n$, the image control module 116 can generate the image data 18.

In this regard, the image control module 116 can perform automatic reconstruction of an initial three dimensional model of the area of interest of the patient 14. Reconstruction of the three dimensional model can be performed in any appropriate manner, such as using algebraic techniques for optimization. Appropriate algebraic techniques include Expectation maximization (EM), Ordered Subsets EM (OS-EM), Simultaneous Algebraic Reconstruction Technique (SART) and total variation minimization. The application to performing a 3D volumetric reconstruction based on the 2D projections allows for efficient and complete volumetric reconstruction.

Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. In this regard, the stylized model can provide additional detail regarding the anatomy of the patient 14, which can enable the user to plan the surgical intervention much more efficiently. The theoretical model can be associated with theoretical image data to construct the theoretical model. In this way, the model or the image data 18 can be built based upon image data acquired of the patient 14 with the imaging system 16. The image control module 116 can output image data 18 to the display device 32a.

The move control module 118 can receive as input the signal 119 from the image control module 116. Based on the signal from the image control module 116, the move control module 118 can set a move signal 126 to the source 36 to move or pivot the source 36 relative to the rotor 40 and the patient 14, and the off-center image control module 110 can also output a move signal 128 to the detector 38 to move or translate the detector 38 relative to the rotor 40 and the patient 14 to capture the x-ray beam from the source 36. In one example, the move signal 126 can comprise an angle of between 0 degrees and 15 degrees for the source 36 to pivot. Similarly, the move signal 128 can comprise between 0 degrees and 15 degrees for the detector 38 to move, translate or pivot relative to the source 36. The move control module 118 can also set a move signal 130 for the rotor 40 to move or rotate the rotor 40 within the gantry 34 relative to the patient 14. In other words, the off-center image control module 110 can control the position of the source 36 and detector 38 relative to the rotor 40 to enable the acquisition of off-center image data as the rotor 40 rotates about the gantry 34. Generally, the rotor 40 can move the source 36 and the detector 38 about 360° around a longitudinal axis 14L of the patient 14 within the gantry 34. The movement of the detector 38 and the source 36 about to the patient 14 can be optimized to allow the imaging system 16 to acquire image data at a plurality of selected locations and orientations relative to the patient 14.

In this regard, the 2D projection image data can be acquired by substantially annular or 360° orientation movement of the source 36 and the detector 38 around the patient 14, as illustrated in the motion profile of the source 36 and detector 38 for image acquisition shown in FIGS. 1, 2 and 7-9. The movement profile of the source 36 and detector 38 relative to the rotor 40 may be a sinusoidal function of the rotor angle, for example. Also, due to movements of the gantry 34, the source 36 and the detector 38 need never move in a pure circle, but rather can move in a spiral helix, or other rotary movement about or relative to the patient 14. Also, the path can be substantially non-symmetrical and/or non-linear based on movements of the imaging system 16, including the gantry 34, the source 36 and the detector 38 together. In other words, the path need not be continuous in that the source 36, the detector 38 and the gantry 34 can stop, move back in the direction from which it just came (e.g., oscillate), etc. in following the optimal path. Thus, the source 36 and the detector 38 need never travel a full 360° around the patient 14 as the gantry 34 may tilt or otherwise move and the source 36 and the detector 38 may stop and move back in the direction it has already passed. Further detail regarding the movement of the source 36 and the detector 38 can be found in U.S. Pat. No. 7,108,421, entitled "Systems and Methods for Imaging Large Field-of-View Objects," filed on Mar. 18, 2003 and incorporated herein by reference.

Thus, the move control module 118 can generate a move profile for each of the source 36, detector 38 and rotor 40, which can allow the acquisition of image data for a particular anatomical location on the patient 14 without requiring the movement of the patient 14 relative to the imaging device 16. The location on the patient 14 can be any selected location on the patient 14 within the gantry 34 for which a 3D volumetric image is desired, regardless of whether the selected location lies along the isocenter of the imaging device 16 (or along the longitudinal axis 14L of the patient 14). This can allow for the acquisition of multiple images of the patient 14 at multiple locations without requiring the repositioning of the patient 14 at the isocenter of the imaging device 16 each time.

Figure 5:
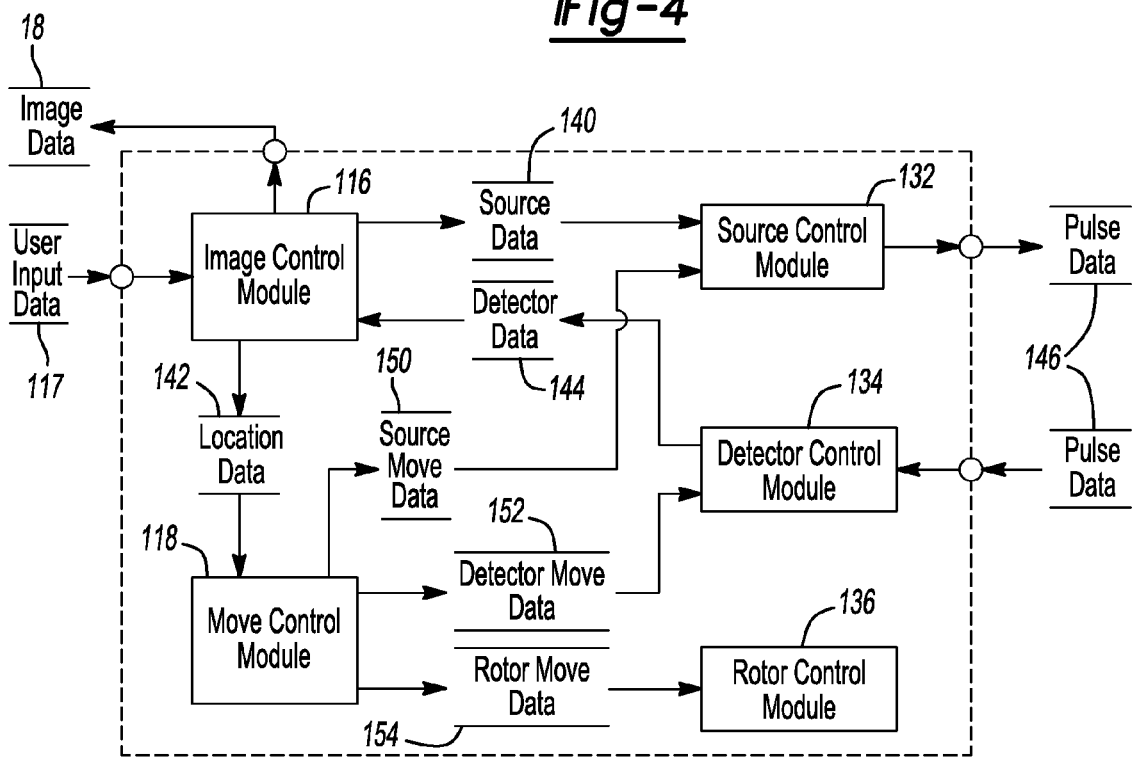
FIG. 5 is a dataflow diagram illustrating an exemplary control system performed by the off-center image control module of FIG. 4.

With reference to FIG. 5, a dataflow diagram illustrates various components of an image control system that can be embedded within the off-center image control module 110. The off-center image control module 110 can control the imaging system 16 to generate the image data 18 for display on the display device 32a and/or display device 20. Various embodiments of the off-center image control system according to the present disclosure can include any number of sub-modules embedded within the off-center image control module 110. The sub-modules shown may be combined and/or further partitioned to similarly generate the image data 18. Further, the off-center image control module 110 can comprise one or more software modules embodied in non-transitory, machine readable code that runs on the processor 102. Inputs to the system can be received from the input device 32c, input device 24, or even received from other control modules (not shown) within the computing system 22 or imaging computing system 32, and/or determined by other sub-modules (not shown) within the off-center image control module 110 (not shown).

With continuing reference to FIG. 5, the off-center image control module 110 can include the image control module 116, the move control module 118, a source control module 132, a detector control module 134 and a rotor control module 136. The image control module 116 can receive as input user input data 117. The user input data 117 can comprise input received from the input device 32c or input device 24. The user input data 117 can comprise a request for the imaging system 16 to gather initial image data for the patient 14 and/or a request to generate a 3D volumetric image of a particular location of the patient 14, which may be positioned off-center or off the longitudinal axis 14L. Based on the user input data 117, the image control module 116 can set source data 140 for the source control module 132 and can set location data 142 for the move control module 118. The source data 140 can comprise a signal to output the x-ray pulses 122, or a signal to power-down the imaging system 16. The location data 142 can comprise the selected location on the patient 14 for 3D volumetric reconstruction, which can be off-center relative to the isocenter of the imaging device 16.

The image control module 116 can also receive as input detector data 144. The detector data 144 can comprise the energy from the x-ray pulses 122 received by the detector 38. Based on the detector data 144, the image control module 116 can generate image data 18, and can output this image data 18 to the display device 32a or display device 20.

The move control module 118 can receive as input the location data 142. Based on the location data 142, the move control module 118 can set source move data 150 for the source control module 132, detector move data 152 for the detector control module 134 and rotor move data 154 for the rotor control module 136. The source move data 150 can comprise a desired angle or degree for the source 36 to pivot relative to the rotor 40 to acquire image data at the desired location on the patient 14. The detector move data 152 can comprise a desired angle or degree for the detector 38 to move or pivot relative to the source 36 and the rotor 40 to acquire image data at the desired location on the patient 14. The rotor move data 154 can comprise a desired movement profile for the rotor 40 to move within the gantry 34 to enable the source 36 and the detector 38 to acquire the image data.

With continued reference to FIG. 5, the source control module 132 can receive as input the source data 140 from the image control module 116 and the source move data 150 from the move control module 118. Based on the source move data 150, the source 36 can pivot relative to the rotor 40 to a desired angle. Based on the source data 140, the source 36 can output pulse data 146. The pulse data 146 can comprise at least one x-ray pulse 122.

The detector control module 134 can receive as input the detector move data 152 and the detector data 144. Based on the detector move data 152, the detector 38 can move, translate or pivot relative to the rotor 40 and the source 38 to detect the pulse data 146. The detector control module 134 can set the detector data 144 for the image control module 116.

The rotor control module 136 can receive as input the rotor move data 154. Based on the rotor move data 154, the rotor 40 can move within the gantry 34 to a desired location in order to acquire the image data at the desired location.

Figure 6:
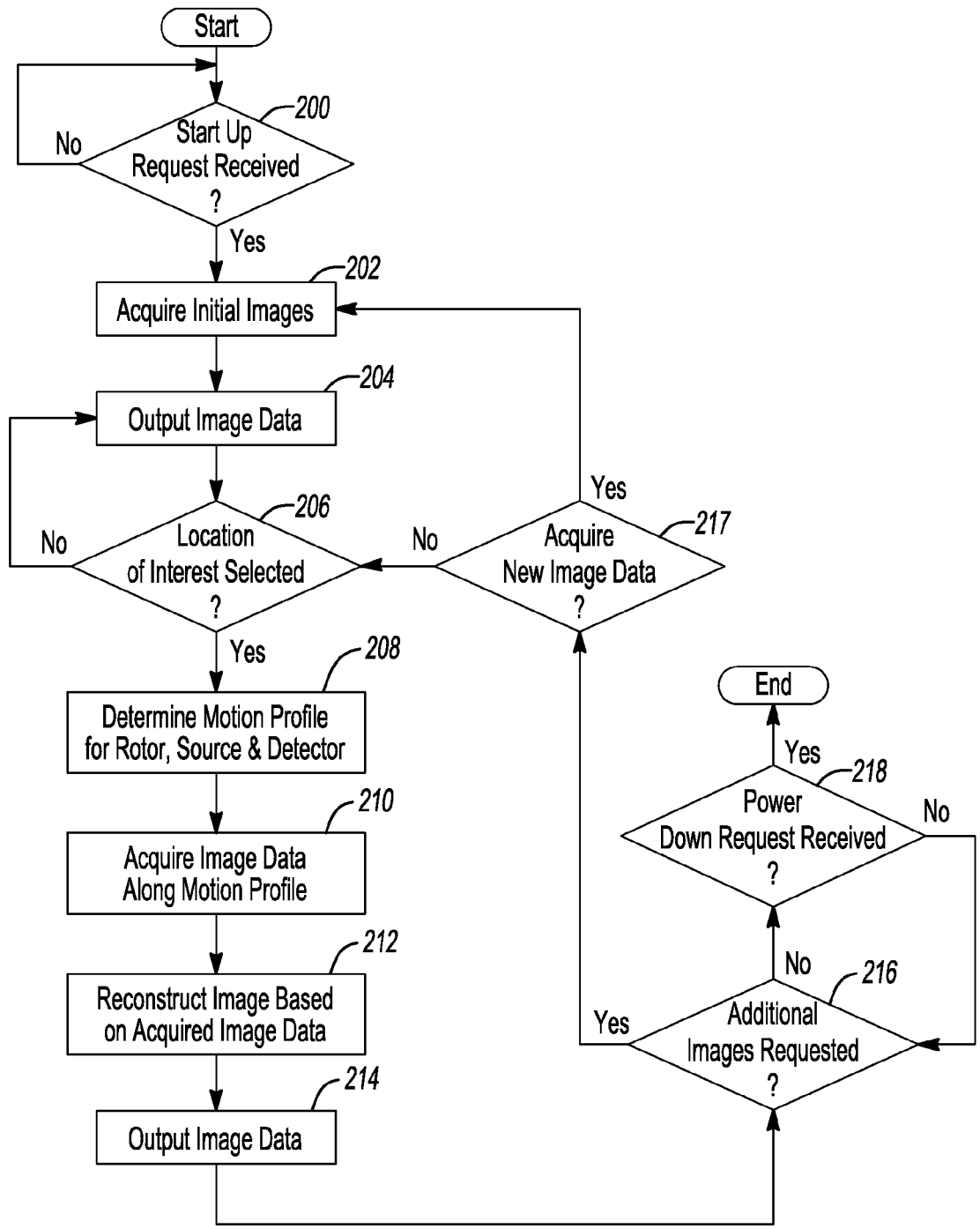
FIG. 6 is a flowchart illustrating a method performed by the off-center image control module.

With reference now to FIG. 6, a flowchart diagram illustrates an exemplary method performed by the off-center image control module 110. It should be noted that the flowchart diagram described herein is merely exemplary, as the off-center image control module 110 could generate the image data 18 in any desired or user requested sequence. With continued reference to FIG. 5, at decision block 200, the method determines if a startup request signal has been received via the input device 32c. If not, the method loops. Otherwise, the method goes to block 202.

At block 202, the method acquires initial image data of the patient 14. As illustrated in FIGS. 10A and 10B, the initial image data can comprise initial 2D images of the patient 14, such as an anterior-posterior (AP) view 300 and a lateral view 302. With reference back to FIG. 6, at block 204, the method can output the acquired initial image data as image data 18 on the display device 32a or display device 20. At decision block 206, the method determines if user input data 117 has been received from the input device 32c, which specifics a particular location of interest on the patient 14 for generating a 3D volumetric image data. The location of interest can be selected from the initial image data, and for example, can be selected by circling or clicking on a portion of the initial image data with the input device 32c. For example, with reference to FIGS. 11A and 11B, the location of interest can be illustrated with a graphical icon 304 superimposed on the image data. If a location of interest has been selected, with reference back to FIG. 6, then the method goes to block 208. Otherwise, the method goes to block 204.

Figure 12:
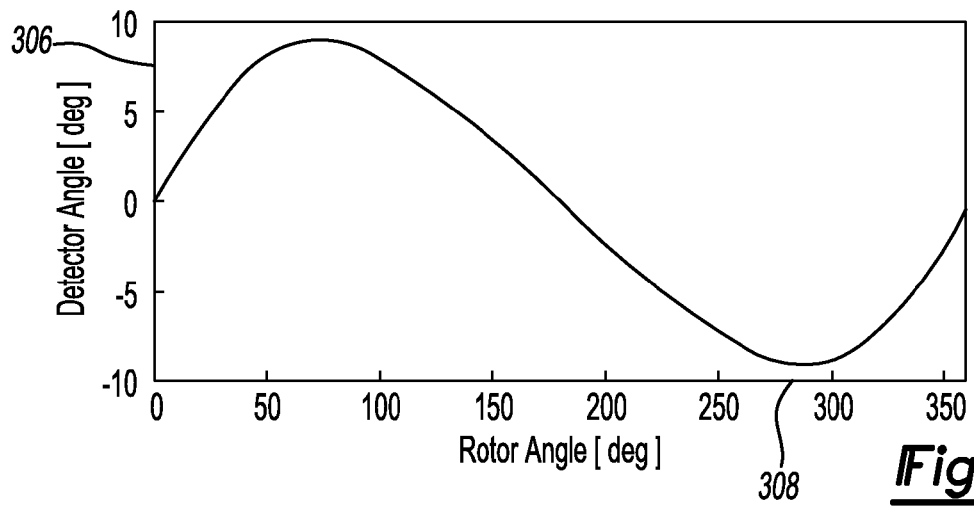
FIG. 12 is an exemplary motion profile for the imaging system of FIG. 1.

At block 208, the method determines the motion profile for the rotor 40, source 36 and detector 38. In one example, with reference to FIG. 12, the motion profile can comprise a graph of detector angle 306 versus rotor angle 308. With reference back to FIG. 6, at block 210, the method acquires image data along the motion profile. In other words, the method controls the movement of the source 36, detector 38 and rotor 40 so that the x-ray pulses 122 output by the source 36 and detected by the detector 38 provide suitable image data for the reconstruction of the 3D volumetric image for the selected location of interest on the patient 14.

Figure 7:
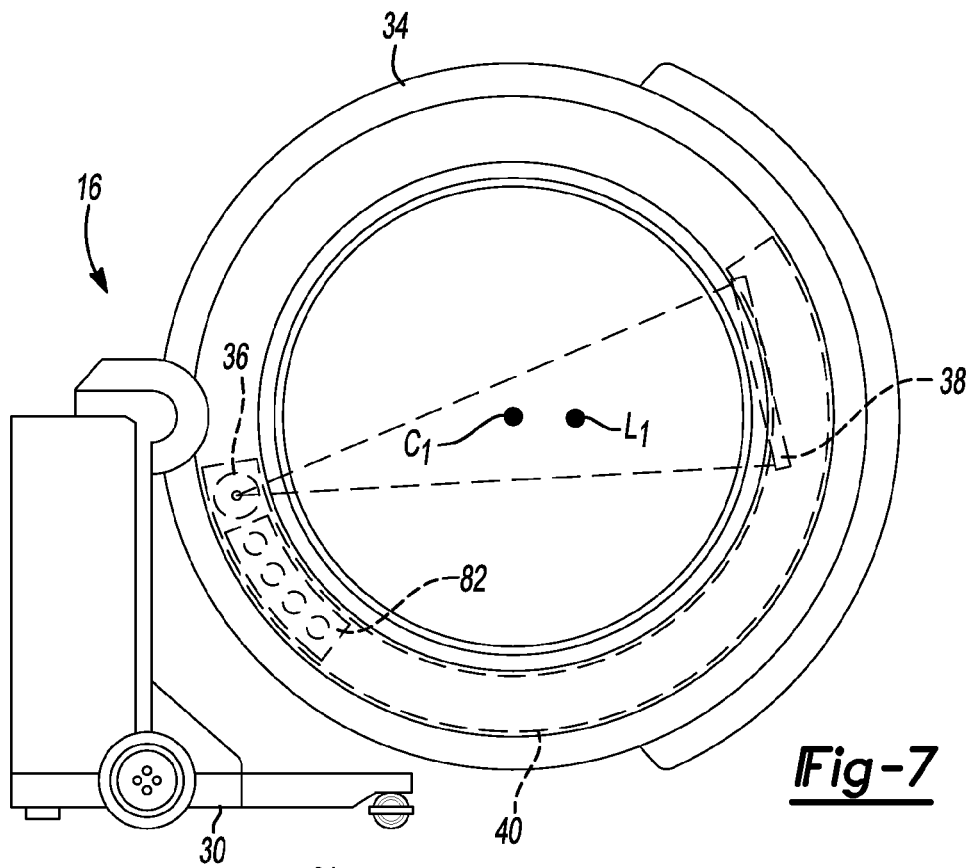
FIG. 7 is a schematic illustration of the imaging system of FIG. 1, with the source and the detector of the imaging system in a third position.
Figure 8:
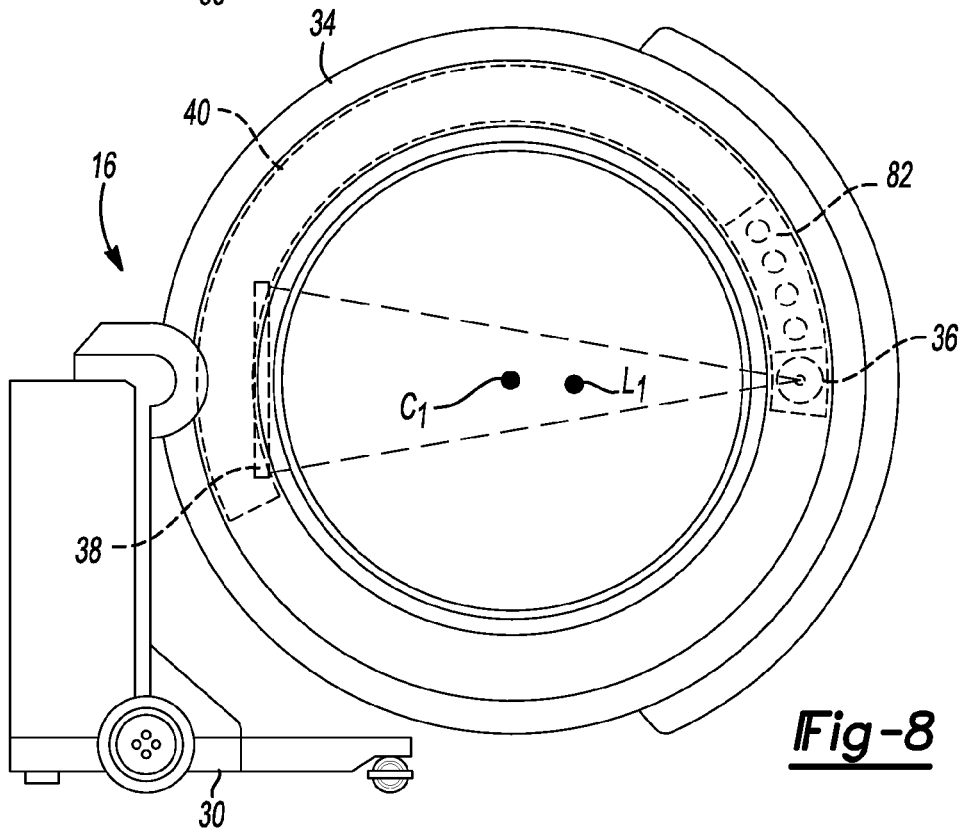
FIG. 8 is a schematic illustration of the imaging system of FIG. 1, with the source and the detector of the imaging system in a fourth position.

An exemplary illustration of the movement of the source 36, detector 38 and rotor 40 along a motion profile for image acquisition is shown in FIGS. 1, 2 and 7-9. For example, as illustrated in FIG. 1, the source 36 and detector 38 can be at a starting or first position. FIGS. 2, 7 and 8 show exemplary intermediate positions for the source 36 and detector 38 relative to the gantry 34 for the generation of off-center image data. FIG. 9 illustrates an exemplary fifth or final position for the acquisition of the off-center image data.

Figure 13A:
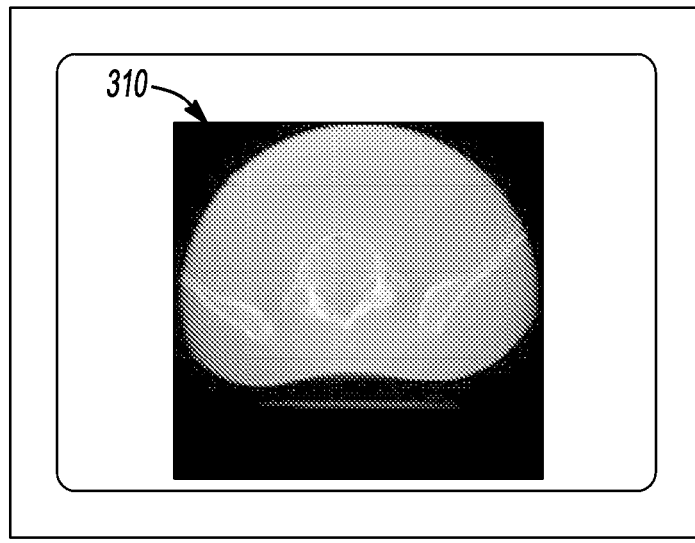
FIG. 13A is an exemplary graphical representation of an image reconstructed based on the selected location of interest from FIG. 10A.
Figure 13B:
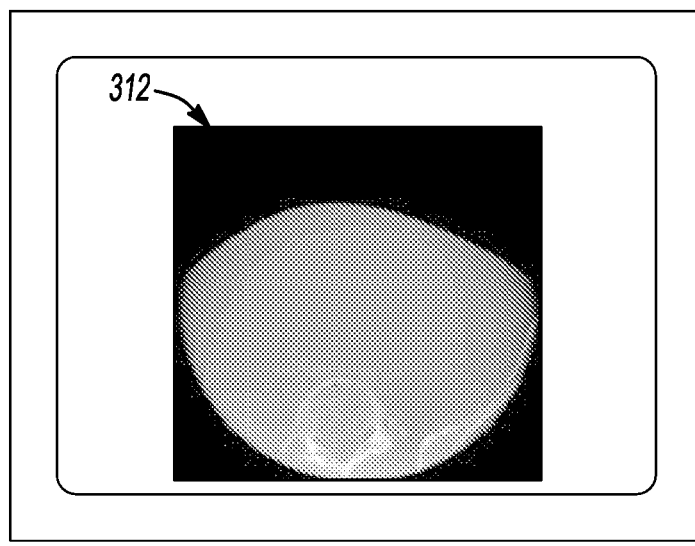
FIG. 13B is an exemplary graphical representation of an image reconstructed without the selected location of interest specified.

At block 212, the method reconstructs the 3D volumetric image data 18 based on the image data acquired along the motion profile. An exemplary image 310 reconstructed based on the selected location of interest is illustrated in FIG. 13A. In comparison, with reference to FIG. 13B, an image 312 reconstructed without selecting a location of interest is shown. At block 214, the method outputs the image data 18 to the display device 32a or display device 20. At decision block 216, the method can determine if additional images are requested by the user via the input device 32c. If additional images are requested, then the method can go to decision block 217. At decision block 217, the method can determine if a request to acquire new image data of the patient 18 has been received. If a request for new image data has been received, then the method goes to block 202. Otherwise, the method goes to decision block 206. At decision block 218, the method can determine if a power down request has been received via the input device 32c. If a power down request has been received, then the method can end. Otherwise, the method can loop to decision block 216.

Thus, the off-center image control module 110 can be used to enable the user to acquire images of the patient 14, which may be off the isocenter of the imaging device 16 without repositioning the patient 14 relative to the imaging device 16. This can enable the user to acquire various images without having to move the patient 14 each time. By not having to move the patient 14 into various positions, the patient experience during the imaging procedure improves.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A system for acquiring image data of a subject with an imaging system, comprising:
    a gantry configured to encompass at least a portion of the subject, the subject positioned along an isocenter of the imaging system;
    a rotor positioned within the gantry and rotatable within the gantry around the isocenter of the imaging system;
    an imager source positioned within and movable relative to the gantry by being moveably coupled to the rotor, the imager source responsive to a signal to output at least one pulse;
    an image detector positioned within and movable relative to the gantry and the imager source by being moveably coupled to the rotor substantially opposed to the imager source, wherein the image detector is to detect the at least one pulse emitted by the imager source; and
    a move control module that sets move data based on a user input for each of the imager source, the image detector, and the rotor that causes the imager source, the image detector, and the rotor to move in a selected motion profile to acquire the image data of a portion of the subject that is off the isocenter of the imaging system;
    wherein the user input includes selecting an area of interest and the move control module is configured to determine movement of each of the imager source, the image detector, and the rotor that causes the imager source, the image detector, and the rotor to move in the selected motion profile to acquire the image data of the portion of the subject to acquire image data for generation of a reconstruction.

2. The system of claim 1, further comprising:
a detector control module that sets detector data based on the detected at least one pulse; and
an image control module that sets the signal for the imager source and receives the detector data;
wherein the image control module is configured to reconstruct image data based on the detector data.

3. The system of claim 2, further comprising:
a user input device configured to generate a signal based on the user input to select imaging a portion of a patient that is off the isocenter of the imaging system.

4. The system of claim 1, further comprising:
a mobile cart configured to allow movement of the gantry from a first location to a second location.

5. The system of claim 4, wherein the gantry is configured to move relative to the mobile cart.

6. The system of claim 1, further comprising:
an imaging system tracker connected to at least one of the gantry, the rotor, the imager source, or the image detector and configured to track the location of the imaging system;
a patient tracker configured to be connected to then allow for a dynamic registration and maintenance of registration of the subject to the image data;
wherein the imaging system tracker and the patient tracker are configured to allow for initial registration of the patient to the image data.

7. The system of claim 6, further comprising:
a navigation system including a navigation interface device and a localizer.

8. The system of claim 7, further comprising:
an instrument; and
a tracking device connected to the instrument;
wherein the navigation system is configured to navigate the instrument.

9. A system for acquiring image data of a subject with an imaging system, comprising:
a mobile cart configured to be moved from a first location to a different second location;
a gantry configured to completely annularly encompass an isocenter and at least a portion of the subject;
a rotor rotatable relative to the gantry around the isocenter of the imaging system;
an imager source moveably coupled to the rotor, wherein the imager source is movable within and relative to the gantry by being moveably coupled to the rotor, the movement of the imager source is due to a signal;
an image detector moveably coupled to the rotor, wherein image detector is movable within the gantry and relative to the imager source by being moveably coupled to the rotor, wherein the image detector is to detect the at least one pulse emitted by the imager source;
a user input system configured to generate a user input signal based on a user selection of an area of interest to move at least one of the gantry, the rotor, the imager source, or the image detector; and
a move control module that sets move data based on the user input from the user input system for each of the imager source, the image detector, and the rotor that causes the imager source, the image detector, and the rotor to move in a selected motion profile to acquire the image data of a portion of the subject that is off the isocenter of the imaging system.

10. The system of claim 9, further comprising:
a subject support configured to support the subject at the isocenter of the gantry.

11. The system of claim 9, further comprising:
an image control module that sets location data for the move control module;
wherein the location data may comprise a selected location on the subject based on an initial image of the subject for a 3D volumetric reconstruction image of the subject.

12. The system of claim 11, wherein the location data may be at the off isocenter of the imaging system.

13. The system of claim 11, wherein the image control module is configured to determine the motion profile for all of the rotor, imager source, and the detector to set the move data.

14. The system of claim 13, wherein the rotor is curved to fit within the gantry and rotate around the isocenter encompassed by the gantry.

15. A system for acquiring image data of a subject with an imaging system, comprising:
a mobile cart configured to be moved from a first location to a different second location;
a gantry configured to completely annularly encompass an isocenter and at least a portion of the subject, wherein the gantry to moveable relative to the mobile cart;
a rotor curved and rotatably moveable within the gantry around the isocenter of the imaging system;
an imager source moveably coupled to the rotor, wherein the imager source is movable within and relative to the gantry by being moveably coupled to the rotor, the movement of the imager source due to a signal;
an image detector moveably coupled to the rotor, wherein image detector is movable within the gantry and relative to the imager source by being moveably coupled to the rotor, wherein the image detector is to detect the at least one pulse emitted by the imager source;
a gantry tracking device connected to the gantry to allow a determination of a location of the gantry;
a subject tracking device to allow a determination of a location of the subject; and
a navigation system configured to determine a location of the gantry tracking device and a location of the subject tracking device to allow for automatic registration of image data that is off the isocenter of the imaging system based on the at least one pulse and the subject.

16. The system of claim 15, wherein the navigation system includes a navigation interface device and a localizer.

17. The system of claim 16, further comprising:
an instrument; and
a instrument tracking device connected to the instrument;
wherein the navigation system is configured to determine a location of the instrument.

18. The system of claim 16, further comprising:
a user input system configured to generate a user input signal to move at least one of the gantry, the rotor, the imager source, or the image detector;
wherein the user input system is configured to receive a user input.

19. The system of claim 18, further comprising:
a move control module that sets move data based on the user input from the user input system for each of the imager source, the image detector, and the rotor that causes the imager source, the image detector, and the rotor to move in a selected motion profile to acquire the image data of a portion of the subject that is off the isocenter of the imaging system.

20. The system of claim 19, further comprising:
a display device configured to display a 3D volumetric reconstruction of a selected location on the subject from the image data.

* * * * *